(12) United States Patent
O'Flynn et al.

(10) Patent No.: US 12,343,481 B2
(45) Date of Patent: *Jul. 1, 2025

(54) URINARY CATHETER ASSEMBLIES HAVING A SLEEVE

(71) Applicant: Hollister Incorporated, Libertyville, IL (US)

(72) Inventors: Padraig M. O'Flynn, Ballina (IE);
James J. Fitzpatrick, Ballina (IE);
Shamsedin Rostami, South Cambridgeshire (GB)

(73) Assignee: Hollister Incorporated, Libertyville, IL (US)

( * ) Notice: Subject to any disclaimer, the term of this patent is extended or adjusted under 35 U.S.C. 154(b) by 16 days.

This patent is subject to a terminal disclaimer.

(21) Appl. No.: 18/484,006

(22) Filed: Oct. 10, 2023

(65) Prior Publication Data

US 2024/0033478 A1 Feb. 1, 2024

Related U.S. Application Data

(60) Continuation of application No. 17/153,184, filed on Jan. 20, 2021, now Pat. No. 11,813,412, which is a
(Continued)

(51) Int. Cl.
*A61M 25/00* (2006.01)
*A61M 25/01* (2006.01)
(Continued)

(52) U.S. Cl.
CPC ...... *A61M 25/008* (2013.01); *A61M 25/0017* (2013.01); *A61M 25/002* (2013.01);
(Continued)

(58) Field of Classification Search
CPC ............ A61M 25/002; A61M 25/0111; A61M 25/0017; A61M 2025/0062; A61M 39/20;
(Continued)

(56) References Cited

U.S. PATENT DOCUMENTS 1,137,086 A 4/1915 Rodiger
2,849,739 A 9/1958 Dresden
(Continued)

FOREIGN PATENT DOCUMENTS

EP 1498151 A2 * 1/2005 .......... A61M 25/002
EP 1982741 B2 * 9/2016 ........ A61M 25/0017
(Continued)

OTHER PUBLICATIONS

Bard Medical "Touchless® Intermittent Kits", website dated May 21, 2013.
(Continued)

*Primary Examiner* — Adam Marcetich
(74) *Attorney, Agent, or Firm* — Cook Alex Ltd.

(57) ABSTRACT

A catheter assembly includes a catheter at least partially positioned within a sleeve. The catheter has a coating, which produces a low-friction surface on the catheter when treated with an activating fluid. A protective tip is connected to the sleeve and has proximal and distal internal seals, with the proximal seal at the proximal end of the tip or between proximal and distal ends of the protective tip. A cap of the assembly has a projection, which is removably received within the protective tip for sealing engagement with the proximal and distal seals to define a fluid reservoir within the protective tip. An activating fluid is contained within the fluid reservoir. The projection may be partially hollow to receive a portion of the catheter. The sleeve may be relatively narrow or at least have a narrowed portion for better distribution of activating fluid to the surface of the catheter.

12 Claims, 3 Drawing Sheets

Related U.S. Application Data division of application No. 14/914,822, filed as application No. PCT/US2014/068299 on Dec. 3, 2014, now Pat. No. 10,946,172.

(60) Provisional application No. 61/911,535, filed on Dec. 4, 2013.

(51) Int. Cl.
*A61M 27/00* (2006.01)
*A61M 39/20* (2006.01)

(52) U.S. Cl.
CPC ......... *A61M 25/0111* (2013.01); *A61M 39/20* (2013.01); *A61M 2025/0062* (2013.01); *A61M 2025/0081* (2013.01); *A61M 27/00* (2013.01)

(58) Field of Classification Search
CPC .. A61M 2210/1089; A61M 2202/0496; A61M 2210/1078; A61M 2210/1085; A61M 25/0113; A61M 39/162; A61M 2025/0175; A61M 2210/1096; A61M 25/013; A61F 5/44; A61F 5/4404; B65D 41/62; B65D 1/0238; B65D 41/023
See application file for complete search history.

(56) References Cited

U.S. PATENT DOCUMENTS

| | | | |
|---|---|---|---|
| 3,187,966 A | | 6/1965 | Klygis |
| 3,421,509 A | | 1/1969 | Fiore |
| 3,640,418 A | | 2/1972 | Wiliams |
| 3,648,704 A | * | 3/1972 | Jackson ............. A61M 25/0111 206/568 |
| 3,762,399 A | * | 10/1973 | Riedell ............... A61M 25/002 600/580 |
| 3,861,395 A | | 1/1975 | Taniguchi |
| 3,968,876 A | | 7/1976 | Brookfield |
| 4,137,916 A | | 2/1979 | Killman et al. |
| 4,204,527 A | * | 5/1980 | Wu ........................ A61M 27/00 600/580 |
| 4,230,115 A | * | 10/1980 | Walz, Jr. ................... A61F 5/44 600/581 |
| 4,834,711 A | | 5/1989 | Greenfield et al. |
| 4,925,448 A | | 5/1990 | Bazaral |
| 5,154,327 A | | 10/1992 | Long |
| 5,209,726 A | | 5/1993 | Goosen |
| 5,217,114 A | | 6/1993 | Gadberry et al. |
| 5,454,798 A | * | 10/1995 | Kubalak ............ A61M 25/0111 604/326 |
| 5,792,114 A | | 8/1998 | Fiore |
| 6,004,305 A | | 12/1999 | Hursman et al. |
| 6,053,905 A | | 4/2000 | Daignault, Jr. et al. |
| 6,090,075 A | | 7/2000 | House |
| 6,375,051 B1 | | 4/2002 | Iverson |
| 6,387,073 B1 | | 5/2002 | Weiler et al. |
| 6,578,709 B1 | | 6/2003 | Kavanagh et al. |
| 7,410,481 B1 | | 8/2008 | Mitts et al. |
| 7,922,712 B2 | | 4/2011 | Tanghoj et al. |
| 8,177,774 B2 | | 5/2012 | House |
| 2001/0001443 A1 | | 5/2001 | Kayerod et al. |
| 2002/0156440 A1 | | 10/2002 | Israelsson et al. |
| 2003/0018302 A1 | | 3/2003 | Kavanagh et al. |
| 2004/0163980 A1 | * | 8/2004 | Tanghoj ............ A61M 25/0028 206/363 |
| 2005/0015076 A1 | | 1/2005 | Giebmeyer et al. |
| 2005/0051572 A1 | | 3/2005 | Vogel et al. |
| 2005/0109648 A1 | | 5/2005 | Kerzman et al. |
| 2005/0199521 A1 | * | 9/2005 | Givens, Jr. .......... A61M 25/002 206/364 |
| 2005/0258131 A1 | | 11/2005 | Moser |
| 2006/0151417 A1 | | 7/2006 | Fuchs |
| 2006/0163097 A1 | * | 7/2006 | Murray ................... B65B 55/22 206/364 |
| 2007/0088330 A1 | * | 4/2007 | House ................ A61M 25/0111 604/327 |
| 2007/0106205 A1 | | 5/2007 | Connell et al. |
| 2008/0097463 A1 | | 4/2008 | House |
| 2009/0000970 A1 | * | 1/2009 | Bordeau ................. A61L 31/04 604/523 |
| 2009/0032536 A1 | | 2/2009 | Hobbs, Sr. |
| 2009/0099531 A1 | * | 4/2009 | Griesbach, III .... A61M 25/002 206/571 |
| 2010/0116695 A1 | | 5/2010 | Bezou et al. |
| 2010/0258568 A1 | | 10/2010 | Frederiksen et al. |
| 2011/0120892 A1 | | 5/2011 | Frederiksen et al. |
| 2011/0230864 A1 | * | 9/2011 | House ................ A61M 25/0111 604/544 |
| 2012/0110951 A1 | | 5/2012 | Van Groningen et al. |
| 2012/0168324 A1 | | 7/2012 | Carleo |
| 2012/0271282 A1 | * | 10/2012 | Schertiger ........... A61M 25/002 206/438 |
| 2013/0026129 A1 | | 1/2013 | Lavaque |
| 2013/0079755 A1 | | 3/2013 | House |
| 2013/0079756 A1 | * | 3/2013 | House ................ A61M 25/0662 604/544 |
| 2013/0144271 A1 | * | 6/2013 | Passadore ................. A61F 5/44 604/328 |
| 2013/0153446 A1 | | 6/2013 | Utas et al. |
| 2014/0194842 A1 | | 7/2014 | Schertiger et al. |
| 2014/0257234 A1 | | 9/2014 | Ma |
| 2014/0360896 A1 | | 12/2014 | Torstensen |
| 2015/0018805 A1 | | 1/2015 | House |

FOREIGN PATENT DOCUMENTS

| | | | | |
|---|---|---|---|---|
| GB | 2284764 A | * | 6/1995 | ......... A61M 25/002 |
| GB | 2 319 507 A | | 5/1998 | |
| WO | WO 99/42155 | | 8/1999 | |
| WO | WO 01/43807 | | 6/2001 | |
| WO | WO 2006/121508 | | 11/2006 | |
| WO | WO 2011/094690 A1 | | 8/2011 | |

OTHER PUBLICATIONS

Vapnek et al., "A Prospective Randomized Trial Of The Lofric Hydrophilic Coated Catheter Versus Conventional Plastic Catheter For Clean Intermittent Catheterization", Journal of Urology, vol. 169, Mar. 2003.

International Search Report and Written Opinion for PCT/US2014/068299, dated Mar. 13, 2015.

Annex to the Notice of Opposition against EP3077031 B1 filed by ConvaTec Limited, filed on Aug. 25, 2021.

* cited by examiner

URINARY CATHETER ASSEMBLIES HAVING A SLEEVE

RELATED APPLICATION

This application is a continuation of U.S. patent application Ser. No. 17/153,184, filed on Jan. 20, 2021, which is a divisional of U.S. patent application Ser. No. 14/914,822, filed on Feb. 26, 2016, now U.S. Pat. No. 10,946,172, which is a U.S. national stage application of PCT Patent Application Serial No. PCT/US2014/068299, filed Dec. 3, 2014, which claims the benefit of and priority of U.S. Provisional Patent Application Ser. No. 61/911,535, filed Dec. 4, 2013, the contents of which are incorporated by reference herein.

DESCRIPTION

Technical Field

The present disclosure generally relates to urinary catheters. More particularly, the present disclosure relates to urinary catheters provided with a protective tip having a fluid reservoir.

BACKGROUND

Intermittent catheterization is a good option for many users who suffer from various abnormalities and pathologies of the urinary system and its nerve supply. Such catheters are typically provided as single use, individually packaged items and may include a gel-lubricant or hydrophilic coating as a lubricant for reducing friction during insertion into the urethra.

Regarding gel-coated catheters, a user applies a gel-lubricant, such as a water-based gel-lubricant, to the surface of the catheter, which reduces friction for ease of insertion into the urethra. In some instances, the gel-lubricant is supplied with the packaged catheter, in which case the gel-lubricant may be applied to the catheter surface just before or during the packaging operation or as the catheter is being inserted by the user.

When a hydrophilic material is used as a lubricant, a thin coating of hydrophilic material is applied to the outer surface of the catheter, and may subsequently be radiation- or heat-cured. When this coating is activated by swelling in contact with a hydrating liquid or wetting agent such as water, it provides a hydrated surface having an extremely low coefficient of friction. One form of this product provides a sterile, individually packaged, single-use catheter in a dry state or condition. The user opens the package, pours water into the package, waits 30 seconds, and then removes the catheter from the package, which is now ready for insertion. Other embodiments provide the amount of wetting agent necessary for immersion of the catheter in a separate compartment of the package. In such embodiments, the user must open the separate compartment of the package to allow the wetting agent to enter the catheter-containing chamber for direct contact with the hydrophilic coated surface. The catheter is then removed from the package and inserted into the urethra. In yet another embodiment, the ready-to-use catheter is provided in a package that already contains enough loose wetting agent to cause it to be immersed. In such an embodiment, the user simply opens the package and removes the catheter therefrom, and then inserts the catheter into the urethra, without the need to add the wetting agent.

A disadvantage of the hydrophilic coated catheters described above is that the immersion liquid has a tendency to spill from the package as the user handles the catheter and tries to remove it for subsequent insertion.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a catheter assembly includes a sleeve, with a catheter at least partially positioned within the sleeve. The catheter has a coating on at least a part of its length, which produces a low-friction surface on the catheter when treated with an activating substance. A protective tip is connected to the sleeve and has proximal and distal internal seals, with the proximal seal positioned at the proximal end of the protective tip or between proximal and distal ends of the protective tip. A cap has a projection removably received within the protective tip for sealing engagement with the proximal and distal seals to define a fluid reservoir within the protective tip. An activating fluid is contained within the fluid reservoir.

In another aspect, a catheter assembly includes a sleeve, with a catheter at least partially positioned within the sleeve. The catheter has a coating on at least a part of its length, which produces a low-friction surface on the catheter when treated with an activating substance. A protective tip is connected to the sleeve and defines a fluid reservoir, with an activating fluid contained therein. A cap has a projection removably received within the protective tip. The catheter assembly also includes at least one fluid-tight film seal, with the film seal being positioned outside of the protective tip and extending between an outer surface of the protective tip and an outer surface of the cap or projection, within the fluid reservoir and extending between an internal surface of the protective tip and an outer surface of the projection, or within the sleeve and connected to a distal end of the protective tip.

DETAILED DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

Figure 1:
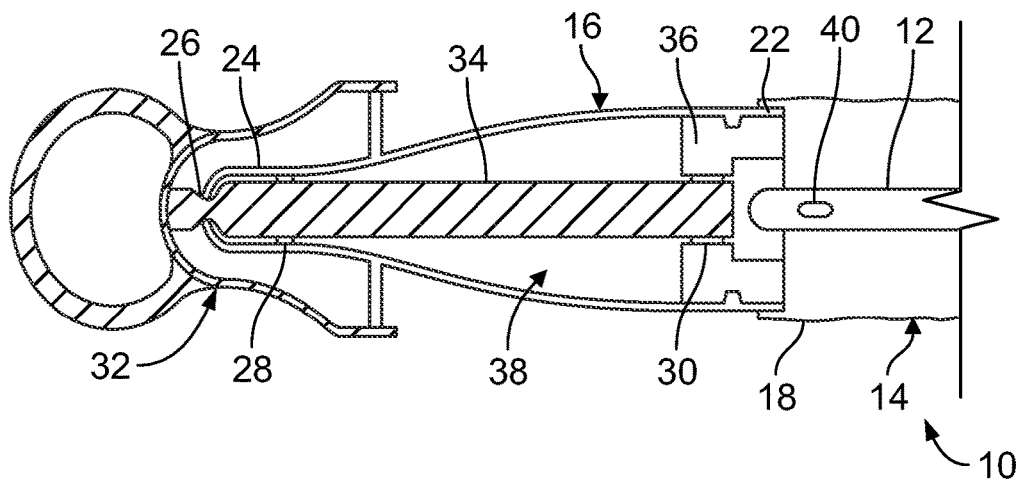
FIG. 1 is a cross-sectional view of a proximal portion of an embodiment of a catheter assembly according to an aspect of the present disclosure.
Figure 2:
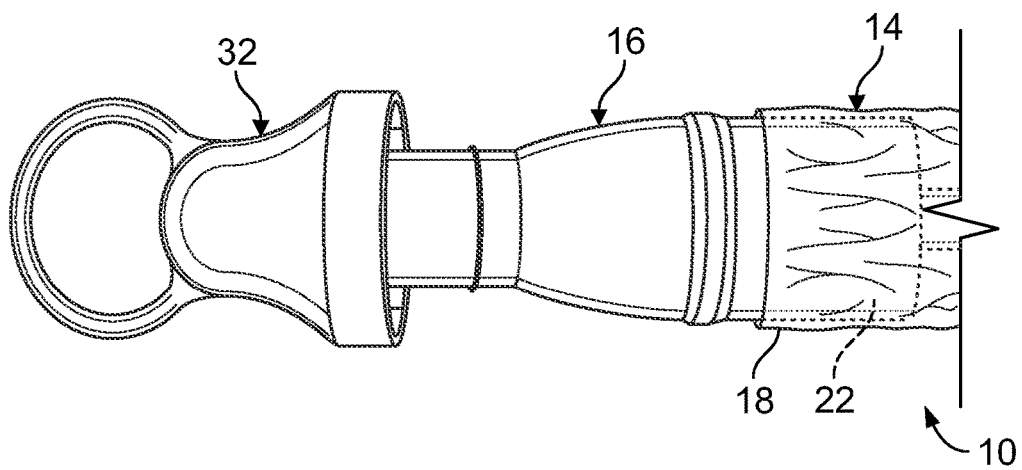
FIG. 2 is a side elevational view of the proximal portion of the catheter assembly of FIG. 1.
Figure 5:
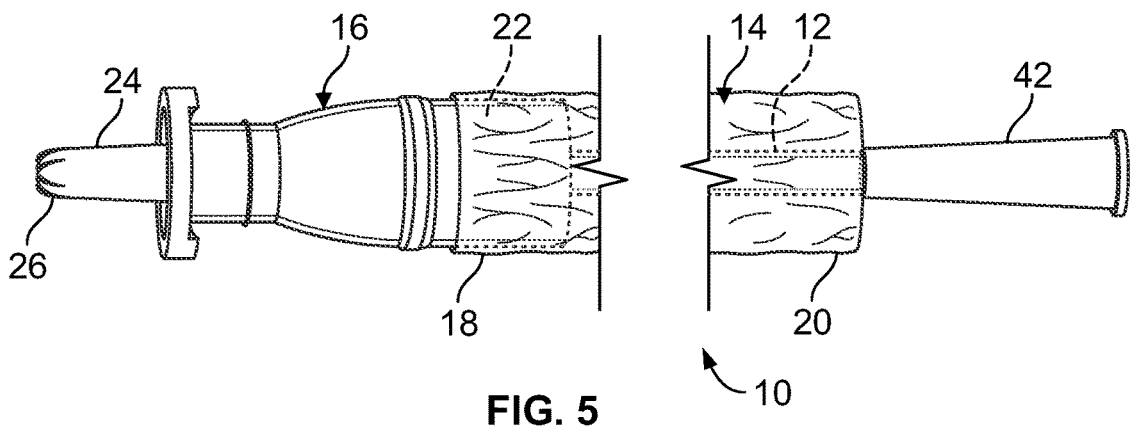
FIG. 5 is a side elevational view of the catheter assembly of FIG. 1.

FIGS. 1 and 2 illustrate an embodiment of a catheter assembly 10, such as a urinary catheter assembly. The catheter assembly 10 may be variously configured without departing from the scope of the present disclosure, but in one embodiment, the catheter assembly 10 includes a catheter 12 (such as a urinary catheter) at least partially positioned within a sleeve 14, which may be defined by a flexible polymeric material (such as, but not limited to, polyurethane) wrapped about the catheter 12. A protective tip 16 is secured or connected to a proximal end 18 of the sleeve 14, with an opposite or distal end 20 of the sleeve 14 (FIG. 5) being sealed or otherwise closed to define a sealed container for the catheter 16.

The protective tip 16 extends between a distal end 22 and a proximal end 24. The protective tip 16 is sealingly connected or secured to the sleeve 14 at or adjacent to the distal end 22 of the protective tip 16. The proximal end 24 of the protective tip 16 may include an aperture or opening 26 that may be moved between a closed configuration (in which the catheter 12 is fully positioned within the sleeve 14 and protective tip 16 and there is no other object positioned within the opening 26) and an open configuration (in which the catheter 12 or any other object is partially positioned within or extending through the opening 26, with a portion of the object positioned within the protective tip 16 and another portion positioned outside of the protective tip 16). In one embodiment, the opening 26 is provided as a slit opening with one or more slits or cuts defining a plurality of deformable petals that may be moved to define the aforementioned open and closed configurations. In other embodiments, the opening may be differently configured, provided that it is configured to allow passage of the catheter therethrough. As will be described in greater detail below, the protective tip 16 may include an internal proximal seal or sealing surface or sealing member 28 and an internal distal seal or sealing surface or sealing member 30 (FIG. 1), with the seals 28 and 30 being spaced from each other and at least the proximal seal 28 positioned between the proximal and distal ends 24 and 22 of the protective tip 16.

The catheter assembly 10 may further include a cap 32 configured to be removably connected to the protective tip 16. As shown in FIG. 1, the cap 32 may be connected to a proximal portion of the protective tip 16 so as to form a substantially fluid- or water-tight seal, which encloses the opening 26 at the proximal end 24 of the protective tip 16. In the illustrated embodiment, the cap 32 includes a projection or extension or plug 34, which is shown as being elongated along a central axis of the cap 32. While the projection 34 is illustrated as having a solid, substantially cylindrical configuration with a substantially uniform outer diameter, it is also within the scope of the present disclosure for the projection 34 to be differently configured (e.g., non-cylindrical).

When the cap 32 has been mounted onto the protective tip 16, the projection 34 is at least partially positioned within the protective tip 16, as shown in FIG. 1. The projection 34 extends through the proximal opening 26 of the protective tip 16 (with the projection 34 holding the opening 26 in an at least partially open configuration) to sealingly cooperate with the protective tip 16 (or a component thereof) to provide the proximal and distal seals 28 and 30. Hence, it can be seen that the projection 34 engages the protective tip 16 (or a component thereof) in at least three locations: at the proximal opening 26, at the proximal seal 28, and at the distal seal 30. It may be preferred for the projection 34 to have a relatively small outer diameter at the portion which is positioned within the proximal opening 26 of the protective tip 16 in order to prevent tip deformation or shape-setting during storage of the catheter assembly 10.

As noted above, the projection 34 sealingly engages the proximal and distal seals 28 and 30 of the protective tip 16, thereby defining a fluid- or water-tight seal at each of the internal seals 28 and 30. The seals 28 and 30 are each configured to press against the outer surface of the projection 34, thereby forming a complete seal around an outer perimeter of the projection 34. To form such a fluid- or water-tight seal, each seal 28, 30 may be configured to define an opening or aperture with a cross-sectional shape that is comparable to the cross-sectional shape of the projection 34. For example, if the projection 34 is substantially cylindrical (as in the illustrated embodiment), with a substantially circular cross-sectional shape, each of the internal seals 28, 30 may substantially annular to define a central circular opening or aperture. In other embodiments, if the cross-sectional shape of the projection 34 is non-circular, one or both of the internal seals 28 and 30 may be configured to define openings or apertures which are similarly non-circularly configured to match the cross-sectional shape of the projection 34.

It may be preferred for the openings or apertures defined by the internal seals 28 and 30 to be slightly smaller than the portion of the projection 34 which is positioned within the opening or aperture when the cap 32 has been mounted onto the protective tip 16. Such a configuration may be preferred in order to promote a fluid- or water-tight seal at each internal seal 28, 30, but it is also within the scope of the present disclosure for the openings or apertures defined by the internal seals 28 and 30 to have a size and shape substantially identical to that of the corresponding portion of the projection 34. If one or both of the internal seals 28 and 30 is configured to define an opening or aperture slightly smaller than the corresponding portion of the projection 34, it may be advantageous for that seal or those seals to be formed of a deformable material to allow the seal to deform outwardly to accommodate the larger cross-section of the projection 34. For example, in one embodiment, the internal seals 28 and 30 of the protective tip 16 may be formed of an elastomeric material (e.g., an O-ring), which provides a fluid- or water-tight seal while being deformable. In other embodiments, different materials such as silicone; the polyether block amide material marketed as PEBAX® by Arkema S.A. of Colombes, France; thermoplastic polyurethanes; thermoplastic elastomers; thermoplastic polyolefins; and the like may be used. It is also within the scope of the present disclosure for the proximal seal 28 to be formed of a different material than the distal seal 30.

The proximal and distal internal seals 28 and 30 may be inner surfaces of the protective tip 16 or may be directly connected to the inner surface of the protective tip 16 or may be connected to the inner surface of the protective tip 16 via an intermediate member. For example, in the illustrated embodiment, the inner surface of the protective tip 16 has a greater diameter at its distal end 22 than at its proximal end 24. In such an embodiment, it may be advantageous for a grommet or spacer or intermediate member 36 to be connected to the inner surface of the protective tip 16 (FIG. 1), with the grommet 36 defining an opening or aperture in which the distal seal 30 may be formed. By providing a grommet 36, the distal seal 30 may be positioned closer to the central axis of the protective tip 16 without increasing the size of the distal seal 30. Alternatively, the grommet 36 itself (as a component of the protective tip 16) may provide an internal seal or sealing surface which sealingly engages the projection 34. The material composition of the grommet 36 may vary without departing from the scope of the present disclosure, but in one embodiment, the grommet 36 is a generally annular member comprised of a generally rigid or semi-rigid material having a relatively low water permeability. For example, the grommet 36 may be made from a thermoplastic elastomer, such as a non-swellable polyolefin material or PEBAX® or the like.

With the cap 32 mounted upon the protective tip 16, the projection 34 forms fluid- or water-tight seals at each internal seal 28, 30. By such a configuration, a fluid reservoir or compartment 38 is defined between the internal seals 28 and 30 of the protective tip 16 (FIG. 1). An activating or hydrating fluid may be contained within the fluid reservoir 38, which fluid is configured to interact with a coating (such as, but not limited to, a hydrophilic coating) on the catheter 12 to provide a lubricious surface to the catheter 12. The nature of the activating fluid may vary depending on the nature of the coating on the catheter 12 but, in one embodiment, the activating fluid is water. The fluid reservoir 38 is at least partially filled with the activating fluid during manufacture (e.g., between 2 and 5 ml of activating fluid) and remains within the fluid reservoir 38 during storage and until the catheter assembly 10 is used, as described below. The fluid reservoir 38 may be filled with the activating fluid by any suitable method, but in one embodiment, the activating fluid may be dispensed into the fluid reservoir 38 while only one of the seals 28 and 30 is in place. In another embodiment, activating fluid in a container (e.g., a water-soluble polymer pouch or container) may be inserted into the fluid reservoir 38, with the container being dissolved (in the case of a water-soluble container) or otherwise manipulated or processed to release the activating fluid into the fluid reservoir 38 after the fluid reservoir 38 has been sealed. Other methods of dispensing activating fluid into the fluid reservoir 38 may be employed without departing from the scope of the present disclosure.

As the fluid reservoir 38 is intended to house the activating fluid during storage of the catheter assembly 10, it may be preferred for the protective tip 16 (or at least the portion defining the fluid reservoir 38) to be formed of a rigid or semi-rigid material having a relatively low water permeability (e.g., polyethylene). Similarly, the projection 34 of the cap 32 is intended to be at least partially positioned within the fluid reservoir 38 during storage of the catheter assembly 10, so it may be advantageous for the cap 32 (or at least the projection 34) to be formed of a rigid or semi-rigid material having a relatively low water permeability. In one embodiment, the fluid reservoir 38 and the projection 34 are formed of the same material, which may also be the same material as is used to form the grommet 36, but in other embodiments, the fluid reservoir 38, the projection 34, and the grommet 36 may be formed of different materials.

Figure 3:
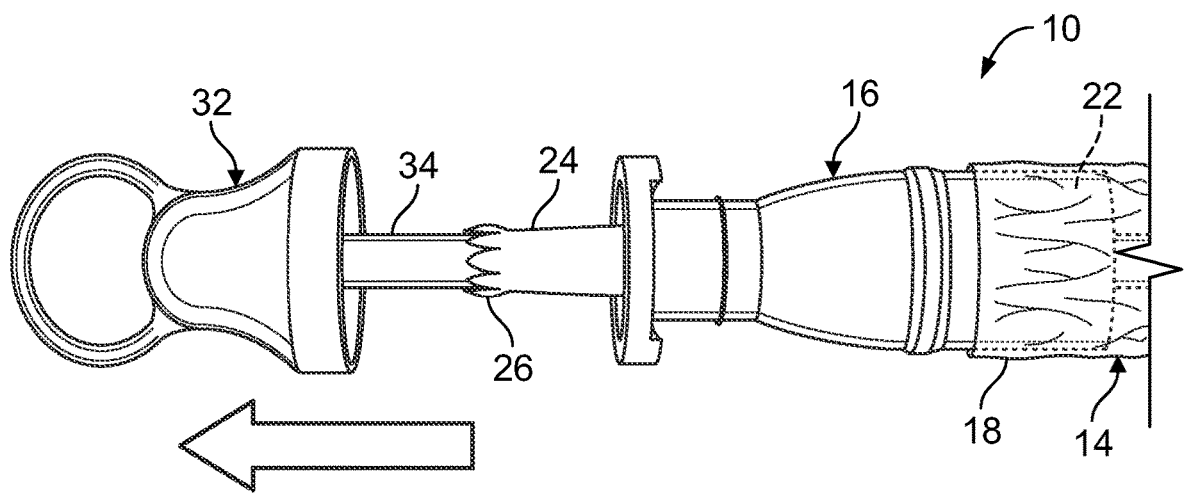
FIG. 3 is a side elevational view of the proximal portion of the catheter assembly of FIG. 1, with a cap of the catheter assembly partially removed from a protective tip of the catheter assembly.

In use, the catheter assembly 10 is provided to a user in the configuration shown in FIGS. 1 and 2. In one embodiment, the catheter assembly 10 may be enclosed within a sealed package or container (not illustrated) that must be opened by the user prior to use of the catheter assembly 10. In other embodiments, the cap 32 and sleeve 14 serve as a sealed package for the catheter 12. When the catheter assembly 10 has been removed from the package (if provided), the user partially withdraws the cap 32 from the protective tip 16 (FIG. 3) so as to disengage the projection 34 from the distal internal seal 30. By so disengaging the projection 34 from the distal internal seal 30, the activating fluid is allowed to flow out of the fluid reservoir 38 and into the sleeve 14 via the opening or aperture defined by the distal seal 30. It may be advantageous for the catheter assembly 10 to be held vertically by the user, with the cap 32 and protective tip 16 pointing upwardly, to promote flow of the activating fluid out of the fluid reservoir 38 and into the sleeve 14. By only partially removing the cap 32 from the protective tip 16, the projection 34 maintains the proximal internal seal 28, thereby preventing the activating fluid from flowing out of the proximal opening 26 of the protective tip 16.

Alternatively, rather than only partially removing the cap 32 from the protective tip 16, the user may completely remove the cap 32 from the protective tip 16 to allow the activating fluid to flow from the fluid reservoir 38 into the sleeve 14. Although there is no proximal internal seal 28 maintained by the projection 34, the proximal opening 26 of the protective tip 16 (in a closed configuration) may provide a fluid- or water-tight seal to prevent the activating fluid from flowing out of the catheter assembly 10.

The activating fluid contacts the hydrophilic coating of the catheter 12 and interacts therewith to form a lubricious coating on the catheter 12. The sleeve 14 is preferably formed of a substantially transparent or translucent material to allow the user to visually confirm that the activating fluid has covered the catheter 12 along the length of the coating. It may also be advantageous for the sleeve 14 to be formed of a flexible material to allow the user to manipulate the catheter 12 through the sleeve 14 to better apply the activating fluid to the coating of the catheter 12. In one embodiment, the sleeve 14 is formed of a soft, hydrophilic material, such as a polyurethane film, although other thin, soft film materials (either vapor permeable or impermeable) may also be used without departing from the scope of the present disclosure.

Figure 4:
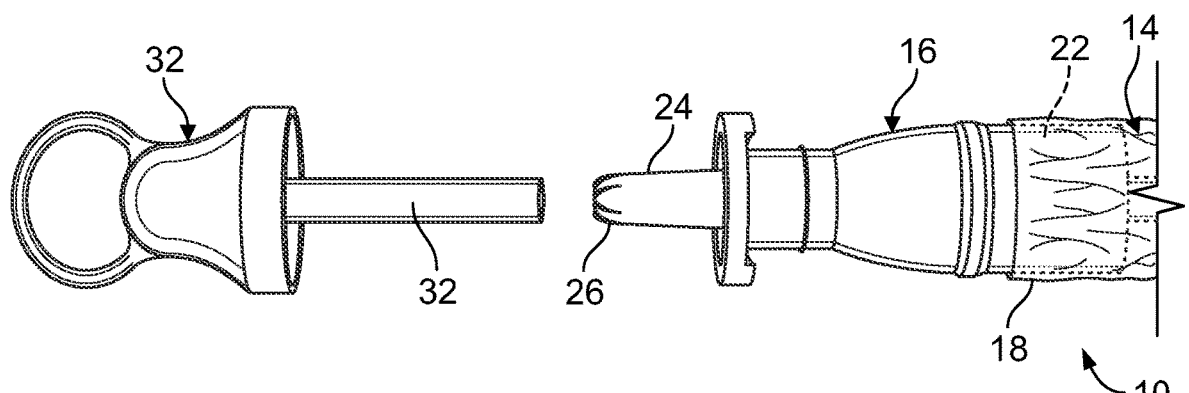
FIG. 4 is a side elevational view of the proximal portion of the catheter assembly of FIG. 1, with a cap of the catheter assembly fully removed from a protective tip of the catheter assembly.

After the catheter 12 has been treated with the activating fluid, the cap 32 may be fully removed from the protective tip 16 (if it has only been partially withdrawn from the protective tip 16), as in FIG. 4, which moves the proximal opening 26 to its closed configuration. Thereafter, the lubricated catheter 12 may be advanced proximally into and through the protective tip 16 to exit the protective tip 16 via the proximal opening 26. If the catheter assembly 10 is provided as a urinary catheter assembly, the proximal end 24 (including the proximal opening 26) of the protective tip 16 may be positioned within the urethra prior to advancing the catheter 12 out of the proximal opening 26 of the protective tip 16. With the proximal end 24 of the protective tip 16 in the urethra, the proximal end of the catheter 12 may be advanced out of the proximal opening 26 of the protective tip 16 and through the urethra until the proximal end of the catheter 12 reaches the bladder. Urine within the bladder flows into the open interior of the catheter 12 via one or more eyes or openings 40 of the catheter 12 (FIG. 1), where it then flows through the catheter 12 and into the sleeve 14. More preferably, rather than allowing urine to flow into the sleeve 14, the distal end of the catheter 12 may include a funnel or drainage device 42 (FIG. 5) that allows urine to drain out of the catheter 12 and into a toilet or other waste receptacle. Thereafter, the catheter 12 may be removed from the urethra, with the catheter assembly 10 and urine being discarded after use.

Figure 6:
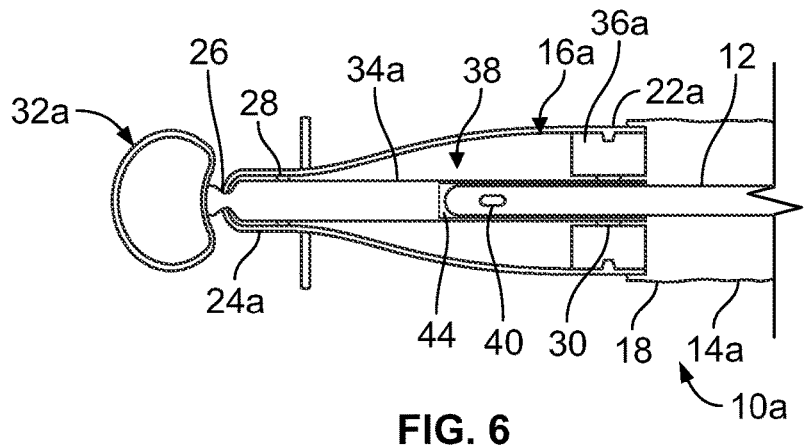
FIG. 6 is a cross-sectional view of a proximal portion of another embodiment of a catheter assembly according to an aspect of the present disclosure.

FIG. 6 illustrates an alternative embodiment of a catheter assembly 10a according to the present disclosure. The embodiment of FIG. 6 is similar to the catheter assembly 10 of FIGS. 1-5, with some differences in the configurations of the protective tip 16a and the cap 32a. In the embodiment of FIG. 6, the protective tip 16a has a generally slimmer configuration than the protective tip 16 of FIGS. 1-5, with the distal end 22a of the protective tip 16a having a diameter that is larger than that of the proximal end 24a, but with the diameters being more similarly sized than in the embodiment of FIGS. 1-5. As in the embodiment of FIGS. 1-5, the distal seal 30 is provided at a grommet or spacer 36a, with the proximal seal 28 being provided at an inner surface of the protective tip 16a. However, it should be understood that the configurations of the internal seals 28 and 30 may vary, as described above with regard to the embodiment of FIGS. 1-5.

As for the cap 32a, it varies from the cap 32 of FIGS. 1-5 in that its projection 34a defines a hollow portion or cavity 44 at a distal portion of the projection 34a. By such a configuration, a proximal end or portion of the catheter 12 may be positioned within the hollow portion 44 of the projection 34a during storage of the catheter assembly 10a, prior to use. Such a configuration may be advantageous in that a shorter sleeve 14a may be employed, thereby decreasing the material cost of the catheter assembly 10a and the storage space required.

It will be seen that the catheter 12 has a smaller diameter than the distal seal 30 in the embodiment of FIG. 6, such that removing the cap 32a results in a gap or separation between the catheter 12 and the distal seal 30. This separation between the catheter 12 and the distal seal 30 allows activating fluid to flow out of the protective tip 16a and into the sleeve 14a when the cap 32a (and, hence, the projection 34a) has been removed, thereby hydrating the portion of the catheter 12 positioned within the sleeve 14a.

Figure 7:
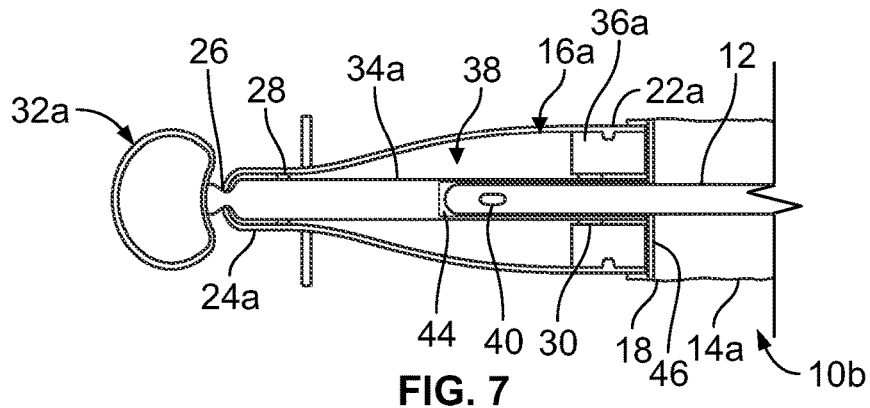
FIG. 7 is a cross-sectional view of a proximal portion of yet another embodiment of a catheter assembly according to an aspect of the present disclosure.

FIG. 7 illustrates a variation of the embodiment of FIG. 6. The catheter assembly 10b of FIG. 7 is substantially identical to the embodiment of FIG. 6, except that it is provided with an additional or third or auxiliary seal or flow-limiting feature 46. In the illustrated embodiment, the third seal 46 is positioned distally of the distal seal 30, at or adjacent to the distal end 22a of the protective tip 16a (i.e., outside and distally of the fluid reservoir 38). The third seal 46 is configured to bear against the catheter 12, thereby forming either a fluid- or water-tight seal therewith or providing a flow-limiting feature. The third seal 46, when providing a fluid- or water-tight seal, helps to maintain the activating fluid within the fluid reservoir 38 after the cap 32a is removed from the protective tip 16a by preventing the activating fluid from flowing into the sleeve 14a. By such a configuration, the activating fluid remains within the fluid reservoir 38, such that the catheter 12 (and the coating thereof) comes into contact with the activating fluid as the catheter 12 is advanced proximally through and out of the protective tip 16a, rather than the activating fluid contacting the coating within the sleeve 14a. On the other hand, if the third seal 46 is configured to provide a flow-limiting feature, at least a portion of the third seal 46 may be spaced away or separated from the outer surface of the catheter 12 to allow a regulated or limited flow of activating fluid into the sleeve 14a when the cap 32a is removed (as in the embodiment of FIG. 6).

The material composition of the third seal 46 may vary without departing from the scope of the present disclosure, but in one embodiment, the third seal 46 is formed of the same material as one or both of the other seals 28 and 30. In other embodiments, the third seal 46 may be formed of a different material than the other seals 28 and 30. Suitable materials for the third seal 46 include, but are not limited to, elastomeric materials, silicone, PEBAX®, thermoplastic polyurethanes, thermoplastic elastomers, thermoplastic polyolefins, and other non-woven fabric materials.

Figure 8:
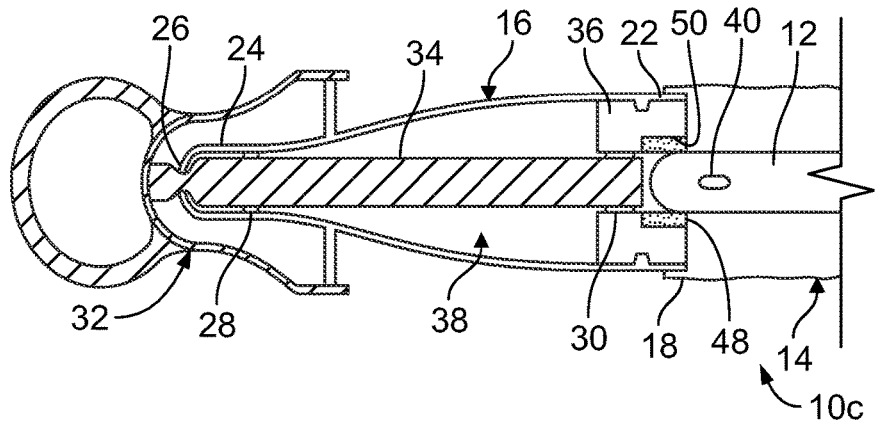
FIG. 8 is a cross-sectional view of a proximal portion of another embodiment of a catheter assembly according to an aspect of the present disclosure.

FIG. 8 illustrates yet another embodiment of a catheter assembly 10c according to the present disclosure. The catheter assembly 10c of FIG. 8 is comparable to the embodiment of FIGS. 1-5, except that it further includes a sponge or absorbent member 48 associated with the protective tip 16 to bear against the catheter 12. In the illustrated embodiment, the absorbent member 48 has a generally annular configuration and is associated with the grommet 36, seated within a counterbore or pocket or cavity 50 at a distal side or end of the grommet 36 (i.e., outside and distally of the fluid reservoir 38). By such a configuration, the absorbent member 48 absorbs and retains a portion of the activating fluid as it flows out of the fluid reservoir 38 and into the sleeve 14. As the catheter 12 is advanced proximally through the protective tip 16, it presses against the absorbent member 48, with the absorbent member 48 applying some of the retained activating fluid to the surface (and, hence, the hydrophilic coating) of the catheter 12. This helps to ensure that activated fluid is applied to the entirety of the coated portion of the catheter 12 as the catheter 12 is advanced out of the protective tip 16. The material composition of the absorbent member 48 may vary without departing from the scope of the present disclosure but, in one embodiment, the absorbent member 48 is formed of a sponge- or foam-like material, such as an open-cell sponge or foam material from foamed polymers (e.g., polyethylene or polyurethane or polyvinyl chloride) or the like.

Figure 9:
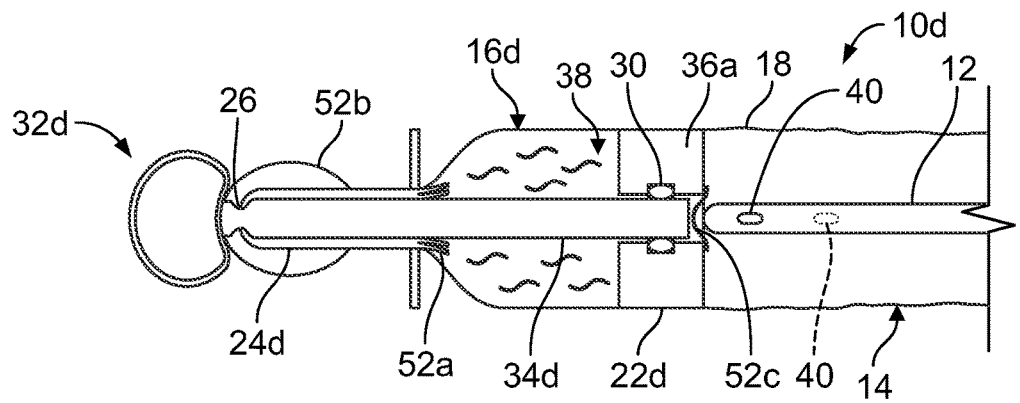
FIG. 9 is a cross-sectional view of a proximal portion of yet another embodiment of a catheter assembly according to an aspect of the present disclosure.

FIG. 9 illustrates an alternative seal configuration. In the catheter assembly 10d of FIG. 9, the projection 34d of the cap 32d is spaced away from the protective tip 16d at the proximal end 24d of the protective tip 16d. A proximal fluid-tight seal is provided between the protective tip 16d and the cap 32d by a fluid-tight film that is sealed to the two components, such as by heat seals. In one embodiment, one or both of the heat seals may be a peelable or breakable, as will be described in greater detail. In the embodiment of FIG. 9, three fluid-tight films 52a, 52b, and 52c are provided, with a distal film 52c providing a distal seal, but it is within the scope of the present disclosure for the catheter assembly 10d to include only one or two such films. For example, the fluid-tight film seal or seals may be configured to provide only a proximal seal, only a distal seal, or both a proximal seal and a distal seal for the fluid reservoir 38.

One of the illustrated films 52a is provided within the protective tip 16d, at or adjacent to the proximal end 24d of the protective tip 16d. The film 52a extends from the inner surface of the protective tip 16d to the outer surface of the cap projection 34d, being connected (e.g., by heat seals) to each component. Another illustrated film 52b is positioned outside of the protective tip 16d, at or adjacent to the proximal end 24d of the protective tip 16d. The second film 52b extends from the outer surface of the protective tip 16d to the outer surface of the cap 32d (or a portion of the projection 34d positioned outside of the protective tip 16d) and is connected (e.g., by heat seals) to each component. The third illustrated film 52c is positioned within the sleeve 14 and is connected (e.g., by a heat seal) to the distal end 22d of the protective tip 16d and/or the grommet 36a of the protective tip 16d, overlaying the opening through which the catheter 12 may be advanced into the fluid reservoir 38. The third film 52c may also be connected (e.g., by a heat seal) to the distal end of the cap projection 34d.

In use, the cap 32d is moved proximally with respect to the protective tip 16d, thereby removing any slack in the films 52a, 52b, and 52c. The slack in the proximal films 52a and 52b allows the projection 34d to separate from the distal seal 30 while the proximal seals provided by the films 52a and 52b remain intact. Preferably, the distal seal provided by the film 52c is broken before the proximal seals are broken, such that the activating fluid flows out of the fluid reservoir 38 (though the opening formerly sealed by the distal film 52c) and into the sleeve 14 to interact with the coating on the catheter 12. In one embodiment, the distal film 52c is connected to the distal end of the cap projection 34d and configured to break or detach from the protective tip 16d or grommet 36a upon sufficient proximal movement of the cap 32d. In another embodiment, the distal film 52c may be configured to be broken by proximal movement of the catheter 12 into contact with the film 52c. In yet another embodiment, the distal film 52c may be configured to dissolve over time (e.g., if the film 52c is formed of a water-soluble material), which allows the activating fluid to be released into the sleeve 14 during storage of the catheter assembly 10d for hydration of the catheter 12 over an extended period of time. Alternatively, the distal film 52c may be configured to only weaken over time, without dissolving, thereby preventing activating fluid from entering the sleeve 14, while also making it easier for a user to break the distal seal.

Depending on the nature of the proximal films 52a and 52b, they may either break upon application of sufficient force or may be peeled off to separate them from one or both of the associated components of the catheter assembly 10d. Breaking/peeling the heat seals of the films 52a and 52b allows for the cap 32d to be fully removed and separated from the protective tip 16d. In one embodiment, the film 52a positioned within the protective tip 16d may be configured to dissolve or weaken over time (e.g., if the film 52a is formed of a water-soluble material), which makes it easier for a user to break the seal and remove the cap 32d immediately prior to use.

Figure 10:
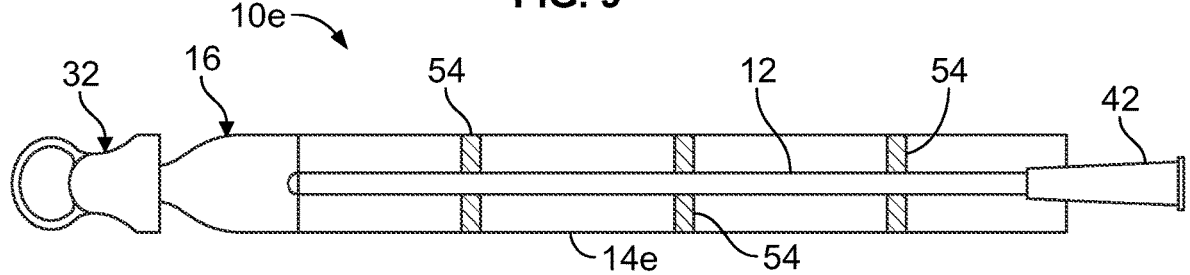
FIG. 10 is a side elevational view of a catheter assembly incorporating an alternative sleeve according to an aspect of the present disclosure.
Figure 11:
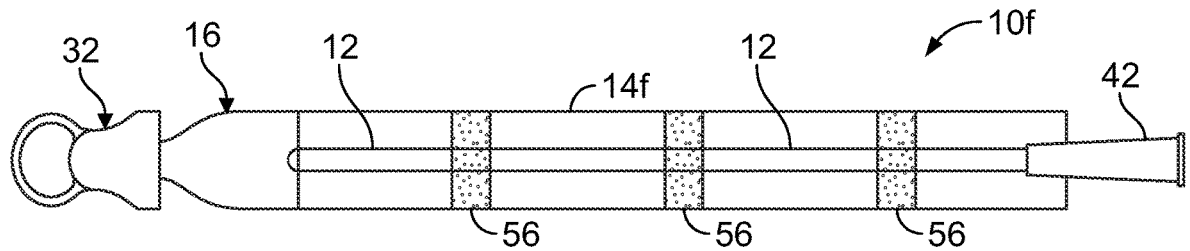
FIG. 11 is a side elevational view of a catheter assembly incorporating another alternative sleeve according to an aspect of the present disclosure.

FIGS. 10 and 11 illustrate catheter assemblies 10e and 10f having alternatively configured sleeves 14e and 14f. The illustrated sleeves 14e and 14f are configured to slow the rate at which activating fluid flows through the sleeve and to extend the time that the activating fluid is in contact with all coated areas of the catheter 12. Either of the sleeves 14e and 14f may be used in combination with any of the catheter assemblies described herein or with other catheter assemblies in which an activating fluid flows through a catheter-containing sleeve.

In the embodiment of FIG. 10, the sleeve 14e is provided with a plurality of constrictions 54, but may have as few as one constriction 54. The constrictions 54 effectively decrease the size of the gap between the sleeve 14e and the catheter 12, thereby preventing the activating fluid from quickly flowing through the sleeve 14e. As the activating fluid flows through the sleeve 14e, it is funneled through the relatively small opening defined by each constriction 54, which causes the activating fluid to remain upstream of each constriction 54 for a longer amount of time, in contact with the coating on the catheter 12. The exact flow rate of the activating fluid through the sleeve 14e and through the opening defined by each constriction 54 may be varied by adjusting the configuration of each constriction 54 (e.g., by increasing or decreasing the size of the opening defined by a constriction 54). The constrictions 54 may be formed by any suitable method, but in one embodiment are formed by a heat sealing procedure that seals together opposing faces of the sleeve 14e.

In the embodiment of FIG. 11, the sleeve 14f is provided with a plurality of absorbent inserts 56, but may have as few as one absorbent insert 56. The absorbent inserts 54 absorb a portion of the activating fluid as it flows through the sleeve 14f. As the catheter 12 is advanced proximally out of the sleeve 14f, it brushes against the absorbent inserts 54, which transfer activating fluid to the coating of the catheter 12 (similar to the action of the absorbent member 48 of FIG. 8). The sleeve 14f may be squeezed at the absorbent inserts 56 to transfer additional amounts of activating fluid from the absorbent inserts 56 to the catheter 12. The configuration of the absorbent inserts 56 may vary, but it may be advantageous for them to be substantially annular and formed from a sponge- or foam-like non-woven fabric material, such as an open-cell sponge or foam material from foamed polymers (e.g., polyethylene or polyurethane or polyvinyl chloride) or the like. The absorbent inserts 56 may be sealed or secured to the sleeve 14f by any suitable means, which may vary according to the material composition of the absorbent inserts 56 and the sleeve 14f.

It should be understood that the methods described herein are merely exemplary, and that the steps described above may be carried out in a different order. Further, other steps may be included when using the devices described herein. Additionally, one or more of the steps described herein in connection with the methods may be omitted or modified without departing from the scope of the present disclosure. Similarly, the systems described herein are merely exemplary, and they may be differently configured (e.g., by combining one or more components of one described embodiment with one or more components of another described embodiment) without departing from the scope of the present disclosure.

Aspects of the present subject matter described above may be beneficial alone or in combination with one or more other aspects. Without limiting the foregoing description, in accordance with one aspect of the subject matter herein, there is provided a catheter assembly, which includes a sleeve with a catheter at least partially positioned therein. There is a coating on at least a part of the catheter which produces a low-friction surface on the catheter when treated with an activating fluid. A protective tip is connected to the sleeve and has proximal and distal internal seals, with the proximal seal being positioned at a proximal end of the protective tip or between proximal and distal ends of the protective tip. A cap includes a projection removably received within the protective tip for sealing engagement with the proximal and distal seals to define a fluid reservoir within the protective tip, with an activating fluid contained within the fluid reservoir.

In accordance with another aspect which may be used or combined with the first aspect, the projection has a substantially uniform outer diameter.

In accordance with another aspect which may be used or combined with the any of the preceding aspects, at least one of the internal seals is formed of a deformable material.

In accordance with another aspect which may be used or combined with the any of the preceding aspects, a grommet is secured to an inner surface of the protective tip, with the grommet defining an opening in which the distal internal seal is positioned.

In accordance with another aspect which may be used or combined with the fourth aspect, a distal side of the grommet defines a pocket, with a generally annular absorbent member at least partially positioned within the pocket.

In accordance with another aspect which may be used or combined with any of the preceding aspects, a distal portion of the projection defines a cavity in which a proximal end of the catheter is positionable.

In accordance with another aspect which may be used or combined with the preceding aspect, a third internal seal is positioned distally of the distal internal seal, with the third internal seal being configured to bear against the catheter.

In accordance with another aspect which may be used or combined with the sixth aspect, a third internal seal is positioned distally of the distal internal seal, with at least a portion of the third internal seal being separated from the catheter to provide a flow-limiting arrangement.

In accordance with another aspect, there is provided a catheter assembly, which includes a sleeve with a catheter at least partially positioned therein. There is a coating on at least a part of the catheter which produces a low-friction surface on the catheter when treated with an activating fluid. A protective tip is connected to the sleeve and defines a fluid reservoir, which contains an activating fluid. A cap includes a projection removably received within the protective tip. At least one fluid-tight film seal is positioned outside of the protective tip and extends between an outer surface of the protective tip and an outer surface of the cap or projection, within the fluid reservoir and extends between an internal surface of the protective tip and an outer surface of the projection, or within the sleeve and connected to a distal end of the protective tip.

In accordance with another aspect which may be used or combined with the preceding aspect, the fluid-tight film seal is peelable or breakable.

In accordance with another aspect which may be used or combined with any of the preceding two aspects, the fluid-tight film seal is positioned outside of the protective tip and extends between the outer surface of the protective tip and the outer surface of the cap or projection. A second fluid-tight film seal is positioned within the fluid reservoir and extends between the internal surface of the protective tip and the outer surface of the projection.

In accordance with another aspect which may be used or combined with any of the ninth through tenth aspects, the fluid-tight film seal is positioned outside of the protective tip and extends between the outer surface of the protective tip and the outer surface of the cap or projection. A second fluid-tight film seal is positioned within the sleeve and is connected to the distal end of the protective tip.

In accordance with another aspect which may be used or combined with any of the ninth through tenth aspects, the fluid-tight film seal is positioned within the fluid reservoir and extends between the internal surface of the protective tip and the outer surface of the projection. A second fluid-tight film seal is positioned within the sleeve and is connected to the distal end of the protective tip.

In accordance with another aspect which may be used or combined with any of the ninth through tenth aspects, the fluid-tight film seal is positioned outside of the protective tip and extends between the outer surface of the protective tip and the outer surface of the cap or projection. A second fluid-tight film seal is positioned within the fluid reservoir and extends between the internal surface of the protective tip and the outer surface of the projection. A third fluid-tight film seal is positioned within the sleeve and is connected to the distal end of the protective tip.

In accordance with another aspect which may be used or combined with any of the ninth through tenth aspects, the fluid-tight film seal is positioned within the sleeve, connected to a distal end of the protective tip, and formed of a water-soluble material.

In accordance with another aspect which may be used or combined with any of the preceding aspects, the sleeve includes a constriction configured to reduce the space between the sleeve and the catheter.

In accordance with another aspect which may be used or combined with the preceding aspect, the sleeve has opposing faces, with the constriction being defined by a heat seal between the opposing faces of the sleeve.

In accordance with another aspect which may be used or combined with any of the preceding two aspects, the sleeve includes a second constriction configured to reduce the space between the sleeve and the catheter.

In accordance with another aspect which may be used or combined with any of the first through fifteenth aspects, an absorbent insert is positioned within the sleeve.

In accordance with another aspect which may be used or combined with the preceding aspect, a second absorbent insert is positioned within the sleeve.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A urinary catheter assembly, comprising:
   a sleeve extending from a proximal end to a distal end; and
   a catheter at least partially positioned within the sleeve, wherein the sleeve includes a plurality of absorbent inserts, with each absorbent insert being positioned within the sleeve between the proximal end and the distal end and spaced away from each of the proximal end and the distal end.

2. The urinary catheter assembly of claim 1, wherein each absorbent insert is substantially annular.

3. The urinary catheter assembly of claim 1, wherein each absorbent insert is formed of a non-woven fabric material.

4. The urinary catheter assembly of claim 1, wherein each absorbent insert is formed of a polymeric foam material.

5. The urinary catheter assembly of claim 1, wherein each absorbent insert is sealed to the sleeve.

6. The urinary catheter assembly of claim 1, wherein the absorbent inserts are substantially identical.

7. The urinary catheter assembly of claim 1, wherein the sleeve includes a proximal absorbent insert, a distal absorbent insert, and an intermediate absorbent insert positioned midway between the proximal absorbent insert and the distal absorbent insert.

8. The urinary catheter assembly of claim 1, further comprising
- a protective tip connected to the proximal end of the sleeve and defining a fluid reservoir, and
- an activating fluid contained within the fluid reservoir, wherein the catheter includes a coating on at least a part of its length which produces a low-friction surface on the catheter when contacted by the activating fluid.

9. The urinary catheter assembly of claim 8, further comprising a cap having a projection removably received within the protective tip, wherein the projection forms a seal with the protective tip to temporarily prevent the activating fluid from flowing out of the fluid reservoir and into the sleeve.

10. The urinary catheter assembly of claim 1, wherein
- the catheter includes a funnel, and
- the distal end of the sleeve is sealed to the funnel.

11. The urinary catheter assembly of claim 1, wherein the catheter is fully positioned within the sleeve.

12. The urinary catheter assembly of claim 1, wherein the catheter is only partially positioned within the sleeve.

* * * * *